United States Patent
Yun

(10) Patent No.: US 7,095,822 B1
(45) Date of Patent: Aug. 22, 2006

(54) NEAR-FIELD X-RAY FLUORESCENCE MICROPROBE

(75) Inventor: Wenbing Yun, Walnut Creek, CA (US)

(73) Assignee: Xradia, Inc., Concord, CA (US)

( * ) Notice: Subject to any disclaimer, the term of this patent is extended or adjusted under 35 U.S.C. 154(b) by 0 days.

(21) Appl. No.: 11/191,611

(22) Filed: Jul. 28, 2005

Related U.S. Application Data

(63) Continuation of application No. 60/591,809, filed on Jul. 28, 2004.

(51) Int. Cl.
*G01N 23/223* (2006.01)
*G01T 1/36* (2006.01)

(52) U.S. Cl. .......................... 378/143; 378/46; 378/49; 977/863; 977/950

(58) Field of Classification Search .................. 378/2, 378/44, 45, 121, 138, 145, 210, 46, 49, 143; 977/949, 950, 849, 863
See application file for complete search history.

(56) References Cited

U.S. PATENT DOCUMENTS

| | | | |
|---|---|---|---|
| 4,958,365 A * | 9/1990 | Sohval et al. ............... 378/122 |
| 5,635,716 A * | 6/1997 | Liu et al. ..................... 250/310 |
| 6,376,267 B1 * | 4/2002 | Noack et al. ................. 438/16 |
| 6,466,309 B1 * | 10/2002 | Kossakovski et al. ........ 356/73 |
| 6,798,863 B1 * | 9/2004 | Sato ............................. 378/46 |
| 2003/0025075 A1 * | 2/2003 | Zaluzec ....................... 250/306 |
| 2005/0220266 A1 * | 10/2005 | Hirsch .......................... 378/43 |

* cited by examiner

*Primary Examiner*—Edward J. Glick
*Assistant Examiner*—Anastasia S. Midkiff
(74) *Attorney, Agent, or Firm*—Houston Eliseeva LLP

(57) ABSTRACT

This invention pertains to an x-ray microprobe that can be placed very close the sample surface. A practical implementation is an x-ray target material integrated to an atomic force microscope (AFM) tip and an electron beam is focused to the target materials to generate x-ray emission. This microprobe can be combined with energy-resolved detector or a fluorescence imaging system for material analysis applications.

18 Claims, 3 Drawing Sheets

NEAR-FIELD X-RAY FLUORESCENCE MICROPROBE

RELATED APPLICATIONS

This application claims the benefit under 35 USC 119(e) of U.S. Provisional Application No. 60/591,809, filed Jul. 28, 2004 which is incorporated herein by reference in its entirety.

BACKGROUND OF THE INVENTION

X-ray fluorescence is a powerful technique for material composition analysis in many industrial and research applications. X-ray fluorescence results when an electron makes a transition from a high atomic orbit to a lower one. With sufficient energy, the excitation radiation, such as x rays, energetic electrons, or ions, eject inner shell electrons by means of photo-electric effect to create a vacancy in the inner shell. This effect results in an unstable atomic state, and the outer shell electrons can transfer to this lower energy shell by a radiative process.

FIG. 1 illustrates the radiative process with respect to the K (left) and L (right) line emissions from a titanium atom. Left: a vacant K shell can be filled by an electron making a transition from L or M shells, resulting the $K_\alpha$ and $K_\beta$ line emissions, respectively. Right: a vacant L shell can be filled by an electron making a transition from M or N shells, resulting in the $L_\alpha$ and $L_\beta$ line emissions, respectively.

The fluorescence x rays have a characteristic energy that is equal to the difference between the two atomic shells, and is often called an emission line. It is characteristic of the particular element. One or a series of emission lines can be used to uniquely identify an element. Transitions to fill a vacancy in K shell results in K-line emission, which is further distinguished by the transition from L shell as $K_\alpha$, and M shell as $K_\beta$, etc. Analogously, transitions to L-shell results in L-line fluorescence emissions. Generally, the transition from the nearest shell has the highest probability and therefore the α lines typically have higher intensity.

FIG. 2A shows x-ray K-shell and L-shell fluorescence emission energy, and FIG. 2B shows the yield as a function of atomic number, i.e., for different elements. From these plots, it is shown that the fluorescence yield generally increases as a function of the atomic number. The K-shell yield is about 1% for elements in organic compounds, C, H, and, O. It increases to about 5% for higher Z elements such as Na, Mg, and P. The yield of L-shell emissions is generally lower than with the K-shell. A few percent can be expected for the middle Z elements such as Mn, Fe, Cu, and Zn.

Besides x-ray excitation, x-ray fluorescence can also be generated by other energetic beams such as ions or electron. X-ray fluorescence from electron excitation is commonly measured with energy-dispersive spectroscopy (EDS) detectors in scanning electron microscopes (SEM) to analyze the material composition of a sample. In addition to the characteristic emission lines, the emission spectra from electron excitation also contain a broad continuum called the Bremstrahlung radiation.

FIG. 3 is a plot of showing the level of the Bremstrahlung radiation relative to the radiation from the emission lines for emission spectrum of bulk titanium excited by 10 kilo electron-Volt electrons. The integrated intensity of the continuum is of similar magnitude to emission lines.

The presence of this background Bremstrahlung radiation makes it extremely difficult to detect minor constituents and trace elements in a sample since their signal is usually buried in the continuum. Consequently electron excitation is generally only used to measure composition with relatively high concentrations of higher than 1%.

The spatial resolution of the EDS technique is limited to about 1 micrometer (μm) by electron scattering inside the sample. In contrast, emission generated by x-ray excitation contains negligible amount of Bremstrahlung background, and consequently, much higher material sensitivity can be achieved: trace element identification with parts per million (ppm) concentrations have been demonstrated.

Current microprobes that "focus" the excitation beam include the focused electron beam (such as in SEM) and the x-ray beam focused by Fresnel zone plates, reflective optics, and near-field capillary optics. The x-ray emitted from the sample is then detected by an EDS or wavelength dispersive spectrometry (WDS) detector, or an x-ray imaging system.

In x-ray imaging systems, the exciting radiation typically comes from a synchrotron radiation source or a rotating anode laboratory source. In many synchrotron radiation source systems, the x-rays are focused to the sample by a zone plate lens. The focused x-ray beam excites x-ray fluorescence emission, which is detected by the EDS detector. In laboratory source systems, the x-ray microprobe consists of an x-ray tube and an x-ray lens (Fresnel zone plate or capillary optics). The probe excites x-ray emission from the sample, which is imaged to a detector by an objective lens (Fresnel zone plate). Note that the spatial resolution of the synchrotron source systems depends entirely on that of the microprobe, in the laboratory source systems, the spatial resolution depends on both the microprobe and the imaging system.

SUMMARY OF THE INVENTION

This invention concerns an x-ray microprobe that can be placed very close the sample surface. In one practical implementation, the probe is an x-ray target that is integrated with an atomic force microscope (AFM) tip or other cantilever structure in which the proximity to the sample surface can be controlled to a high level of accuracy. An electron beam is focused to the target to generate x-ray emissions. This microprobe can be combined with energy-resolved/wavelength-resolved detector or a fluorescence imaging system for material analysis applications.

In general according to one aspect, the invention features an x-ray probe system. This system comprises a target supported adjacent a sample surface and a beam source for generating an energetic beam to generate x-ray emissions from the target to probe the sample.

In many implementations, the x-ray target is made from titanium (Ti), chromium (Cr), copper (Cu), molybdenum (Mo), silver (Ag), tantalum (Ta), tungsten (W), or gold (Au). The beam source generates a focused electron beam, x-ray beam, or ion beam.

Preferably, the energetic beam has an energy of between 1 and 150 keV, and the target has a thickness of between 10 nm and 10 μm.

The target is supported close to the sample surface. Usually the distance is between 1 and 100 μm.

In one embodiment, the target is integrated to a probe tip of an atomic force microprobe (AFM).

Generally, a proximity control system is used with the target to control a distance between the target and a surface of the sample. It senses the distance and then feed the sensed distance to an actuation system to enable closed-loop control of the distance.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention concerns an x-ray microprobe that has an x-ray target that is placed in close proximity to the sample and specifically the sample surface. An energetic beam, for example a focused electron beam, focused x-ray beam, or focused ion beam, then strikes the target to generate the x-ray emission.

The emitted x-rays are then used as a microprobe to excite fluorescence emission from the sample.

Figure 1:
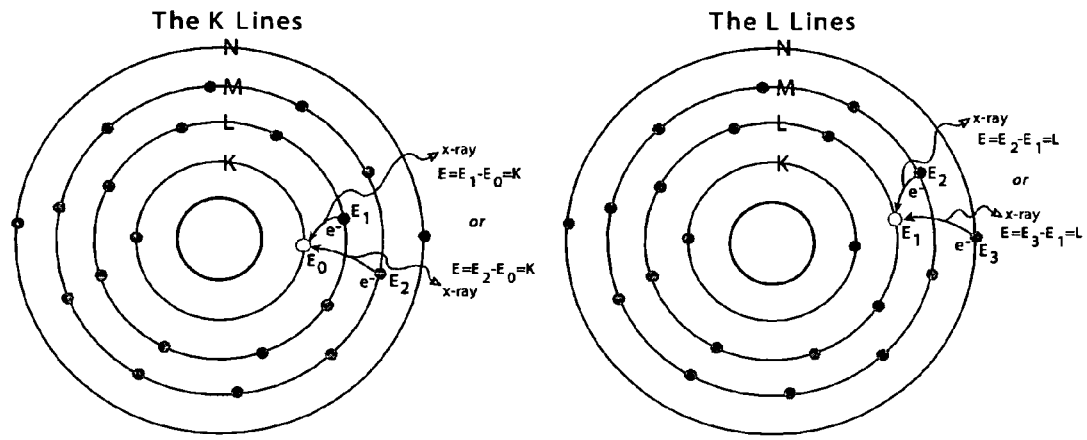
FIG. 1 is a schematic diagram illustrating the x-ray fluorescence process in atoms.
Figures 2A, 2B:
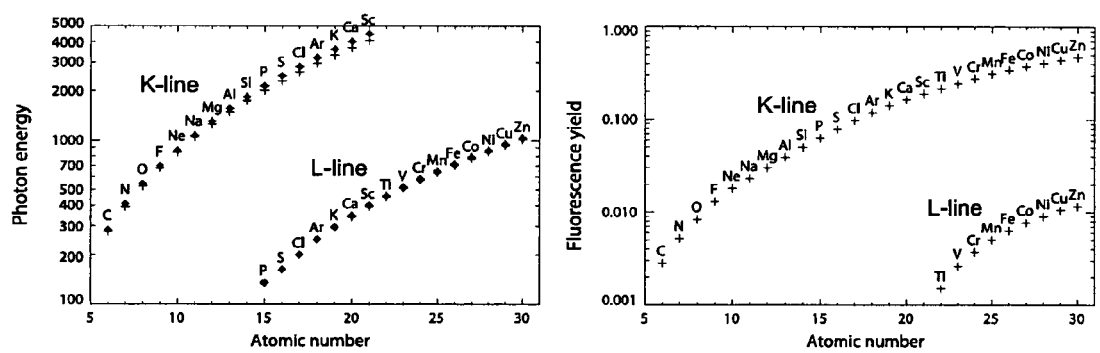
FIG. 2A is a plot of photon energy as a function of atomic number for x-ray fluorescence processes.
FIG. 2B is a plot of fluorescence yield as a function of atomic number.
Figure 3:
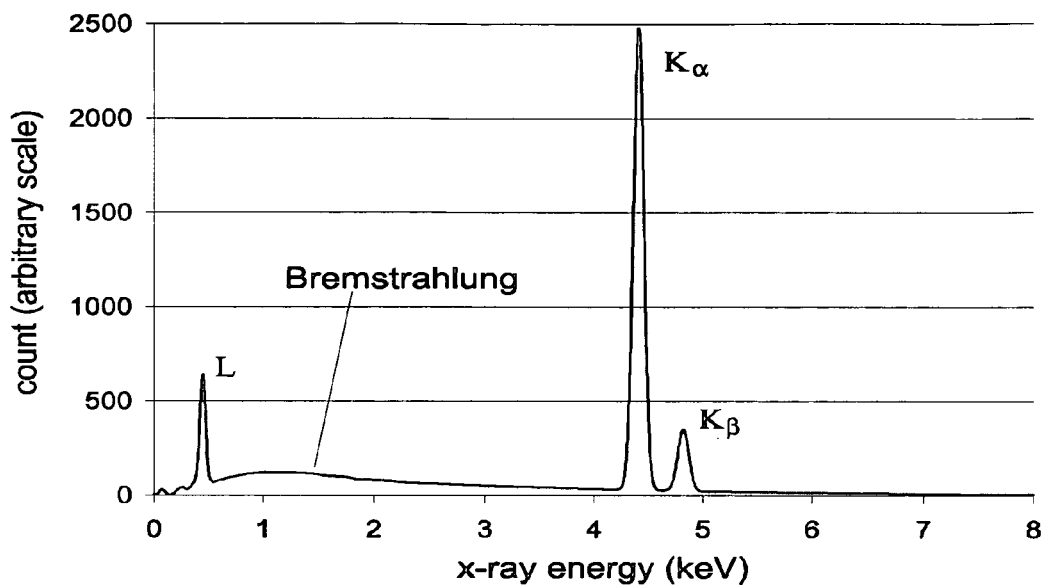
FIG. 3 is a plot of radiation count as function of energy showing the emission spectrum of bulk titanium excited by 10 keV.
Figure 4:
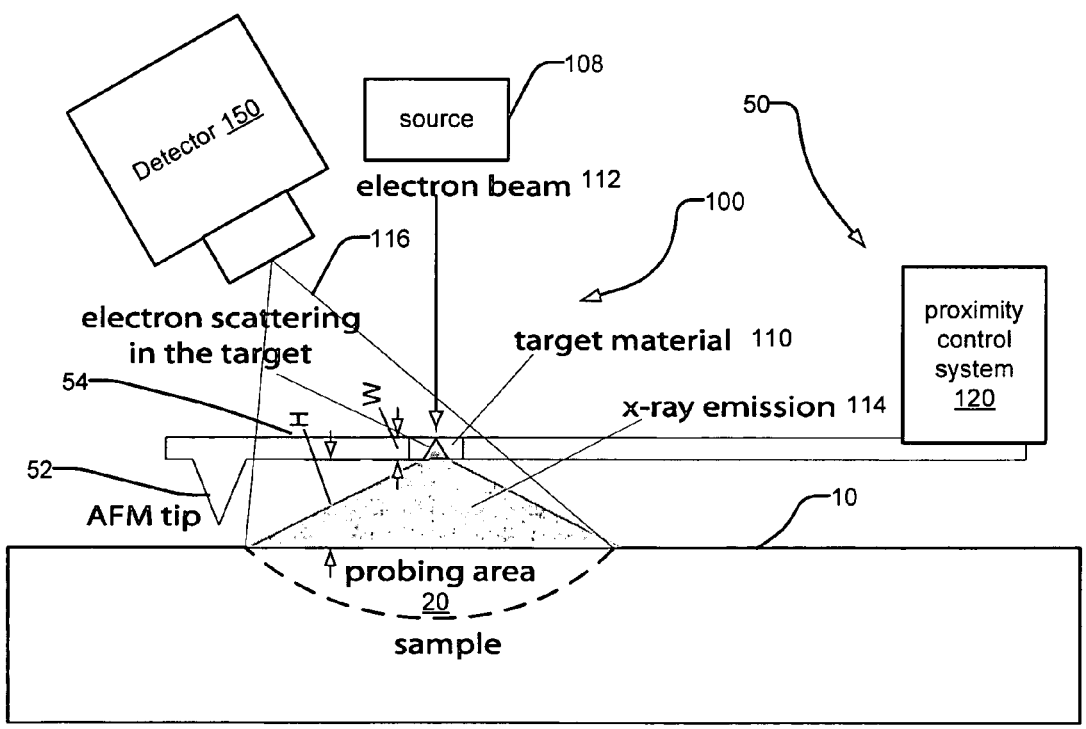
FIG. 4 is a side plan schematic view of an atomic force microprobe with integrated x-ray microprobe system, according to the present invention.
Figure 5:
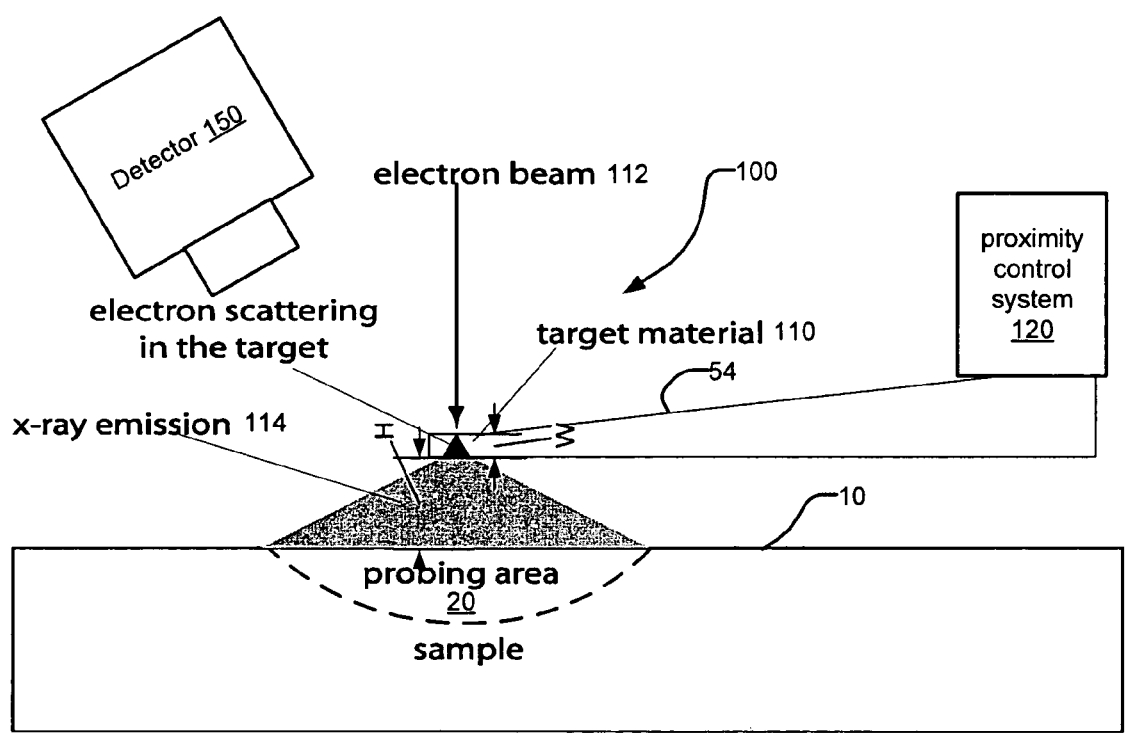
FIG. 5 is a side plan schematic view of an x-ray microprobe system, according to another embodiment.

FIG. 4 illustrates an AFM 50 with integrated x-ray microprobe 100 that has been constructed according to the principles of the present invention.

The AFM 50 comprises a tip 52, such as a tiny shard of diamond, that has been bonded to a cantilevered arm 54, such as a strip of gold foil. More commonly, the tip/arm assembly is fabricated from silicon or silicon nitride using micro electromechanical systems (MEMS) fabrication processes.

In typical operation, the tip 52 at the end of the cantilever arm 54 was pressed against the surface of the sample 10 while the sample was scanned beneath the tip. The force between tip 52 and sample 10 is measured by tracking the deflection of the cantilever 54. This can be done by monitoring a tunneling current or using different optical systems such as interferometers, lasers, or detector arrays.

According to the invention, a target material 110 is integrated with the atomic force microscope (AFM) tip/arm assembly. In one example, the arm 54 is fabricated from the target material. In another example, the arm 54 and/or the tip 52 comprises a section including the target material 54. For example, the target material 110 is deposited, such as sputtered or plated, onto the arm 54.

The target material 110 is bombarded by the energetic beam 112 from an energetic beam source, such as electron gun, 108 to generate x rays 114, which will irradiate a certain probing area 20 that is under or adjacent to the target 110 of the tip 52/arm 54 assembly.

In other implementations, the beam source 108 generates a focused x-ray beam or a focused ion beam.

The fluorescence emission 116 from probing area 20 is then detected by a detector 150. In one embodiment, the detector 150 is an energy dispersive detector such as EDS or WDS detector. On other embodiments, the fluorescence emission 116 is imaged by an x-ray imaging system using an x-ray lens, e.g., zone plate, onto a spatially resolved detector system. One example of such an x-ray detector system is disclosed in U.S. patent application Ser. No. 10/157,089, filed May, 29, 2002, by Wenbing Yun, et al., entitled Element-Specific X-Ray Fluorescence Microscope and Method of Operation, which is incorporated herein by this reference in it entirety.

In one embodiment, the microprobe system 100 is integrated into the AFM tip and the target material 110 is titanium (Ti), chromium (Cr), copper (Cu), molybdenum (Mo), silver (Ag), tantalum (Ta), tungsten (W), or gold (Au). The target material thickness W is preferably between 10 nanometers (nm) and 10 μm thick. The electron beam 112 preferably has energy of between 1 and 150 keV. The distance H between the bottom surface of the target material and the sample 10 is between 1 and 100 μm. In the illustrated implementation, this distance corresponds to the height of the arm 54. In other implementations, it corresponds to the height of the tip 52.

In the preferred embodiment, the invention utilizes a proximity control system 120 of the AFM 50 to control the distance between the target material 110 and the probing area 20 of the sample 10. In this way, the proximity or distance H between the irradiated region of the target material 110 and the probing area 20 of the sample 10 is controlled to a high level of accuracy and precision. Specifically, the proximity control system preferably comprises a proximity detector for detecting the distance H and an arm actuator that controls the distance between the arm/tip assembly and the sample 10. The combination of the proximity detector and actuator 120 provides feedback control of the distance. In a common implementation, the proximity detector is a force sensor, i.e. the bending of the cantilever arm 54, and the actuator is piezo electric device.

FIG. 6 shows another embodiment of the microprobe system.

Specifically, a small point target material 110 is controlled to be brought close to the sample surface of the sample 10 and is then bombarded by the electron beam 112. The target material is usually titanium (Ti), chromium (Cr), copper (Cu), molybdenum (Mo), silver (Ag), tantalum (Ta), tungsten (W), and gold (Au). The target material thickness can be between 10 nm and 10 μm thickness. The electron beam 112 usually has an energy of between 1 and 150 keV. The distance H between the target material 110 and the sample 10 is preferably between 1 and 100 μm.

In some implementations, the entire cantilever arm 54 is constructed from the material of the target 110. In other implementations, the cantilever arm 54 is constructed from another material such as a material compatible with microelectromechanical systems (MEMS) fabrications techniques such as silicon or silicon nitride. Desired target material is then preferably fabricated on top of the cantilever, such as by electroplating or other deposition technique.

In either case, similar to the AFM embodiment, a proximity control system 120 is used to control the distance H between the arm 54 and specifically the target area 110 and the surface of the sample. In one example, the proximity control system 120 comprises a detector for sensing the distance and actuator for controlling the distance as previously described.

In both embodiments, the x-ray fluorescence emission from the sample can be detected by and EDS or WDS detector or can be imaged by an x-ray lens, including Fresnel zone plate lens or total-reflective optics and multilayer reflective optics, to a spatially, two dimensionally resolved detector system.

While this invention has been particularly shown and described with references to preferred embodiments thereof, it will be understood by those skilled in the art that various changes in form and details may be made therein without departing from the scope of the invention encompassed by the appended claims.

What is claimed is:

1. An x-ray probe system, comprising:
   a target supported adjacent a sample surface which is integrated into a probe tip of an atomic force microprobe (AFM); and
   a beam source for generating an energetic beam to generate x-ray emissions from the target to probe the sample.

2. A system as claimed in claim 1, wherein the x-ray target is made from titanium (Ti), chromium (Cr), copper (Cu), molybdenum (Mo), silver (Ag), tantalum (Ta), tungsten (W), or gold (Au).

3. A system as claimed in claim 1, wherein the beam source generates a focused electron beam.

4. A system as claimed in claim 1, wherein the beam source generates a focused x-ray beam.

5. A system as claimed in claim 1, wherein the beam source generates a focused ion beam.

6. A system as claimed in claim 1, wherein the energetic beam has energy of between 1 and 150 keV.

7. A system as claimed in claim 1, wherein the target has a thickness of between 10 nm and 10 µm.

8. A system as claimed in claim 1, wherein a distance between the target and the sample is between 1 and 100 µm.

9. A system as claimed in claim 1, further comprising a proximity control system for controlling a distance between the target and a surface of the sample.

10. A system as claimed in claim 1, further comprising a cantilever system for supporting the target adjacent the sample.

11. A system as claimed in claim 10, wherein the cantilever system is fabricated from the material of the target.

12. A system as claimed in claim 10, wherein the target is deposited on the cantilever.

13. A system as claimed in claim 10, further comprising a proximity control system for controlling a distance between the cantilever system and a surface of the sample.

14. A system as claimed in claim 1, further comprising a detector for detecting fluorescence emission from the sample.

15. A system as claimed in claim 14, wherein the detector comprises an energy dispersive detector.

16. A system as claimed in claim 14, wherein the detector comprises an wavelength dispersive spectrometry detector.

17. A system as claimed in claim 14, wherein the detector comprises an x-ray lens and a spatially resolved detector system.

18. A system as claimed in claim 14, wherein the detector comprises a zone plate lens and a spatially resolved detector system.

* * * * *